United States Patent
Patrascu et al.

(10) Patent No.: US 7,594,979 B2
(45) Date of Patent: Sep. 29, 2009

(54) PURIFICATION OF PROPYLENE OXIDE RESULTING FROM EPOXIDATION OF PROPYLENE WITH HYDROGEN PEROXIDE

(75) Inventors: Renate Patrascu, Stade (DE); Sabrina Astori, Venice (IT); Meinolf M. Weidenbach, Drochtersen (DE)

(73) Assignee: Dow Global Technologies, Inc., Midland, MI (US)

( * ) Notice: Subject to any disclaimer, the term of this patent is extended or adjusted under 35 U.S.C. 154(b) by 531 days.

(21) Appl. No.: 10/541,171

(22) PCT Filed: Mar. 4, 2004

(86) PCT No.: PCT/US2004/006529

§ 371 (c)(1),
(2), (4) Date: Jun. 30, 2005

(87) PCT Pub. No.: WO2004/083196

PCT Pub. Date: Sep. 30, 2004

(65) Prior Publication Data

US 2006/0113180 A1    Jun. 1, 2006

Related U.S. Application Data

(60) Provisional application No. 60/455,506, filed on Mar. 18, 2003.

(51) Int. Cl.
 *B01D 3/38* (2006.01)
 *B01D 3/42* (2006.01)
 *C07D 301/32* (2006.01)
(52) U.S. Cl. .............................. 203/1; 203/76; 203/79; 203/96; 203/99; 203/DIG. 19; 549/531; 549/541
(58) Field of Classification Search ................. 203/1–3, 203/74–80, 95–99, DIG. 19, DIG. 23; 549/531, 549/541
See application file for complete search history.

(56) References Cited

U.S. PATENT DOCUMENTS

| | | | |
|---|---|---|---|
| 3,337,425 | A | 8/1967 | Binning et al. |
| 3,464,897 | A | 9/1969 | Jubin, Jr. et al. |
| 3,578,568 | A | 5/1971 | Washall et al. |
| 3,843,488 | A | 10/1974 | Schmidt et al. |
| 4,140,588 | A | 2/1979 | Schmidt |
| 4,971,661 | A | 11/1990 | Meyer et al. |
| 5,000,825 | A | 3/1991 | Shih et al. |
| 5,006,206 | A | 4/1991 | Shih et al. |
| 5,116,465 | A | 5/1992 | Yeakey et al. |
| 5,116,466 | A | 5/1992 | Marquis et al. |

(Continued)

FOREIGN PATENT DOCUMENTS

EP    1003701 B1    5/2000

(Continued)

*Primary Examiner*—Virginia Manoharan

(57) ABSTRACT

A process of separating a purified propylene oxide from a crude epoxidation product produced, preferably, in an epoxidation reaction of propylene with hydrogen peroxide. The process involves removing bulk water, bulk methanol, and unreacted propylene from the crude epoxidation product and thereafter subjecting the resulting propylene oxide product to extractive distillation with water as an extraction solvent. Under distillation conditions, including a bottoms temperature of greater than about 55° C. and less than about 75° C., an overhead or side-cut distillate stream containing a purified propylene oxide is obtained with low yield loss of propylene oxide to propylene glycols and other glycol heavies. The purified propylene oxide can be further purified in a finishing distillation to obtain propylene oxide meeting commercial grade purity requirements.

23 Claims, 1 Drawing Sheet

U.S. PATENT DOCUMENTS

Figure 1:
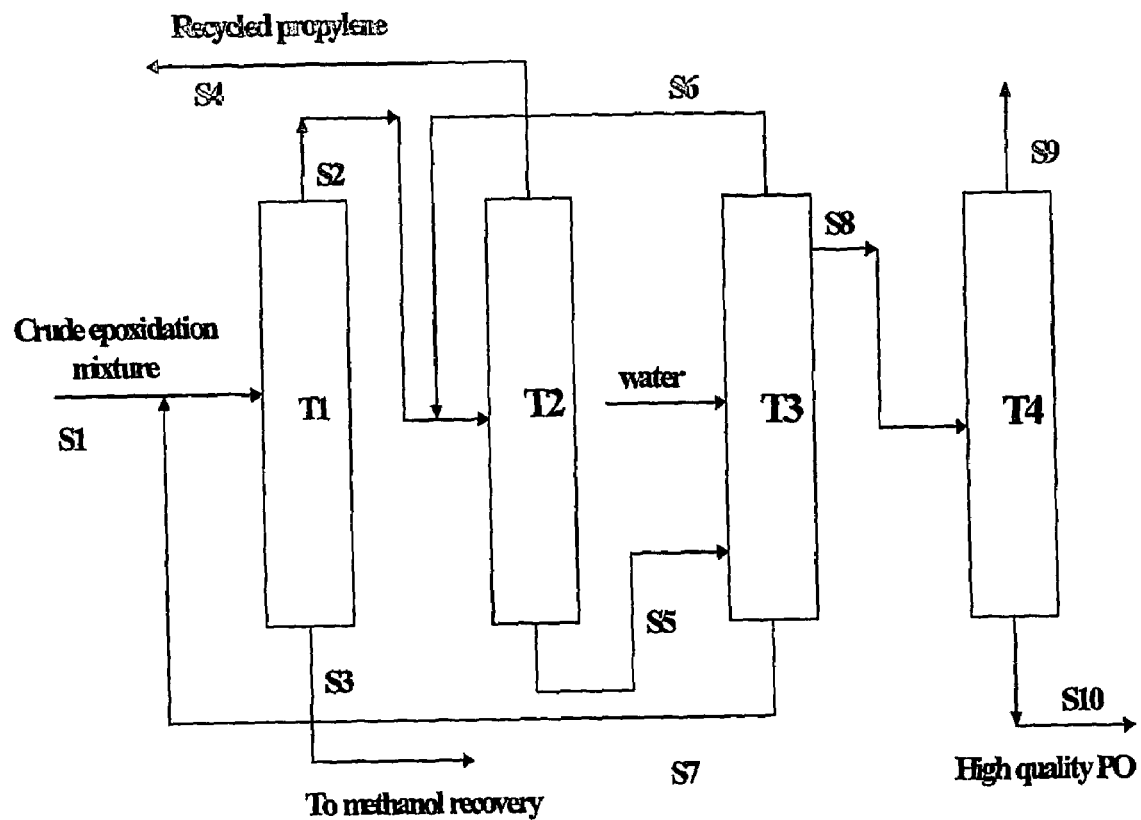

| | | |
|---|---|---|
| 5,116,467 A | 5/1992 | Marquis et al. |
| 5,129,996 A | 7/1992 | Shih et al. |
| 5,133,839 A | 7/1992 | Shih et al. |
| 5,139,622 A | 8/1992 | Marquis et al. |
| 5,145,561 A | 9/1992 | Marquis et al. |
| 5,145,563 A | 9/1992 | Culbreth, III et al. |
| 5,145,803 A | 9/1992 | Daimer et al. |
| 5,146,804 A | 9/1992 | Carmillet |
| 5,160,587 A | 11/1992 | Marquis et al. |
| 5,340,446 A | 8/1994 | Nelson et al. |
| 5,453,160 A | 9/1995 | Peters et al. |
| 5,464,505 A | 11/1995 | Peters et al. |
| 5,620,568 A | 4/1997 | Smith et al. |
| 5,830,324 A * | 11/1998 | Downs et al. ............... 203/1 |
| 5,849,938 A | 12/1998 | Rueter et al. |
| 6,024,840 A | 2/2000 | Rueter |
| 7,323,579 B2 * | 1/2008 | Gobbel et al. ............... 549/541 |
| 2003/0040637 A1 | 2/2003 | Hofen et al. |
| 2005/0082159 A1 * | 4/2005 | Oku et al. ..................... 203/68 |

FOREIGN PATENT DOCUMENTS

| | | |
|---|---|---|
| EP | 1003733 B1 | 5/2000 |
| EP | 1009746 B1 | 6/2000 |
| EP | 1122248 A1 | 7/2000 |
| IT | 1290847 B1 | 12/1996 |
| WO | WO 99/07690 | 2/1999 |
| WO | WO 01/57010 | 9/2001 |
| WO | WO 02/00634 | 1/2002 |
| WO | WO 02/14298 | 2/2002 |

* cited by examiner

PURIFICATION OF PROPYLENE OXIDE RESULTING FROM EPOXIDATION OF PROPYLENE WITH HYDROGEN PEROXIDE

CROSS REFERENCE TO RELATED APPLICATION

This application claims the benefit of U.S. Provisional Application Ser. No. 60/455506, filed Mar. 18, 2003.

BACKGROUND OF INVENTION

This invention pertains to a process of recovering propylene oxide in purified form from an epoxidation reaction product, preferably, a reaction product obtained from the epoxidation of propylene with hydrogen peroxide in the presence of a titanium-containing zeolite catalyst.

Propylene oxide finds utility as a starting material in the preparation of polypropylene polyether polyols, which find utility in the manufacture of polyurethane polymers. Propylene oxide used for such purposes is required to meet strict purity specifications, so as to avoid disadvantageous effects in downstream polyurethane products.

Epoxidation processes comprising the reaction of propylene with hydrogen peroxide in the presence of titanium-containing zeolite catalysts are known in the art, as illustrated, for example, in international patent publication WO-A1-02/14298 (Enichem S. P. A.) Such processes are typically conducted in the presence of a reaction solvent, preferably, methanol, which tends to promote high catalyst activity and selectivity. Such processes produce water as a co-product and minor amounts of glycols, glycol ethers, acetaldehyde, acetone, and propionaldehyde as by-products. Accordingly, a crude propylene oxide product stream obtained from such epoxidation processes contains in addition to the propylene oxide substantial quantities of reaction solvent, typically methanol, and water, as well as impurity amounts of glycols, acetaldehyde, acetone, and propionaldehyde.

The purification of the crude propylene oxide product is known to be difficult. It is especially difficult to remove methanol and acetaldehyde to a high degree of efficiency. Nevertheless, commercial grade propylene oxide requires that the product contains no greater than 10 parts per million (ppm) methanol; no greater than 100 ppm water; and no greater than 30 ppm aldehydes.

The purification of propylene oxide has been considered in the prior art. Certain disclosures, represented by U.S. Pat. No. 4,140,588, teach the extractive distillation of propylene oxide with water for the purpose of removing contaminating quantities of methanol and acetone. Typically, a crude feed comprising from 92 to 99 percent propylene oxide and small quantities of water, methanol, and acetone is fed to a lower portion of an extractive distillation zone. Water is fed at a higher point on the column, and the extractive distillation is operated at a bottoms temperature ranging from 60° C. to 100° C. An overhead distillate is obtained comprising a substantially pure propylene oxide; while a bottoms fraction is obtained comprising predominantly methanol, water, acetone, and disadvantageous amounts of propylene oxide and propylene glycol. Typically, the disclosed process suffers a yield loss of propylene oxide that is greater than 1 percent and as high as 2.5 percent.

Other art, represented by U.S. Pat. No. 5,849,938 and EP-B1-1,009,746, discloses the separation of propylene oxide, acetaldehyde, and methanol by extractive distillation using water or propylene glycol as extraction solvent. The crude epoxidation mixture, containing from 2 to 10 percent propylene oxide, 50 to 85 percent methanol, 10 to 30 percent water, and 0.01 to 0.1 acetaldehyde by weight, is introduced into an intermediate section of the distillation tower. A bottoms temperature from 90° C. to 120° C. is maintained, such that a bottoms stream is obtained containing methanol, water, any further extractive solvent, and a substantial portion of the acetaldehyde. A purified propylene oxide is obtained; but disadvantageously, the concentration of methanol in the purified propylene oxide remains higher than acceptable for most applications. Moreover, the references do not address the yield loss of propylene oxide in the extractive distillation process due to side-reactions of propylene oxide with the extractive solvent and methanol in the feed.

Other art, represented by EP-A1-1,122,248 and WO-A1-01/57010, discloses the work-up of an epoxidation product stream containing propylene, propylene oxide, methanol, and an organic solvent, such as methanol. The work-up comprises separating the product stream in a pre-evaporator such that between 20 and 60 percent of the amount of organic solvent and more than 95 percent of the propylene oxide fed is removed with the overhead product. The residue of the organic solvent and over 90 percent of the water fed is contained in the bottom product. Thereafter, the propylene remaining in the overhead is stripped in a C3 stripper. The recovered product mixture is thereafter subjected to extractive distillation using a polar solvent, such as water, so as to obtain a purified propylene oxide in the overhead product and methanol and polar solvent in the bottoms product. The references are silent with respect to various aspects of the extractive distillation, the quality of purified propylene oxide obtained, and the yield loss of propylene oxide.

Other art, represented by EP-B1-1003733 and U.S. Pat. No. 6,024,840, discloses the separation of methanol and acetaldehyde from a crude epoxidation reaction product comprised of 2 to 10 percent propylene oxide, 60 to 85 percent methanol, 10 to 25 percent water, 0.01 to 0.1 percent acetaldehyde, and 0.01 to 0.1 propylene, by weight. It is taught to fractionate the crude epoxidation reaction product at a reflux: distillate ratio generally of from 10:1 to 30:1 to obtain a bottoms stream comprising methanol, water, and at least 99 percent of the acetaldehyde, and to obtain an overhead stream comprising propylene oxide, propylene, and residual methanol, but substantially devoid of water and acetaldehyde. It is further disclosed to remove propylene from the overhead stream in a second distillation. Thereafter, the resulting propylene oxide stream devoid of propylene is taught to be subjected to extractive distillation using a polar solvent, such as propylene glycol, generally at a bottoms temperature of from 80° C. to 110° C. From the extractive distillation, a bottoms stream is obtained containing the extractive solvent, methanol, water, and other impurities; while a purified propylene oxide is obtained as overheads. Disadvantageously, the high bottoms temperature of the extractive distillation might cause unacceptable yield loss of propylene oxide due to by-product formation. Moreover, the concentration of methanol illustrated in the purified propylene oxide is too high for most applications.

In consequence of the above, a need exists for improvements in the separation and purification of propylene oxide reaction products, preferably those obtained from the epoxidation of propylene with hydrogen peroxide. An efficient and cost-effective separation scheme that produces commercial grade propylene oxide meeting required purity standards would be highly desirable. Due to the high boiling point of propylene glycol, it would be more desirable if the separation method did not require this component as an extraction solvent. It would be even more desirable if the separation method did not produce unacceptable losses of propylene oxide due to by-product formation with methanol or extractive solvents in the crude product.

SUMMARY OF THE INVENTION

This invention provides for a novel process of separating a purified propylene oxide from a propylene oxide reaction product, the process comprising:

(a) introducing a reaction product comprising from about 65 to 88 percent propylene oxide, from about 10 to 35 percent methanol, and less than 0.5 percent water, by weight, into a bottom section of an extractive distillation zone;

(b) introducing water into an upper-half section of said extractive distillation zone;

(c) removing from said extractive distillation zone under distillation conditions a bottoms stream comprising propylene oxide, water, and methanol, (d) removing from said extractive distillation zone under distillation conditions, an overhead or side-cut stream comprising a purified propylene oxide essentially devoid of methanol and water; the extractive distillation conditions being sufficient to maintain a yield loss of propylene oxide of less than about 0.3 mole percent.

For the purposes of this invention, the term "yield loss of propylene oxide" will refer to the mole percentage of propylene oxide lost in the extractive distillation process to glycols, such as propylene glycol and glycol heavies (e.g., glycol ethers), based on the total moles of propylene oxide fed to the extractive distillation.

In a related aspect of this invention, the overhead or side-cut stream obtained from step (d) hereinabove, may optionally be subjected to distillation to recover a purified propylene oxide product meeting commercial grade purity standards.

The novel process of this invention may be beneficially employed to separate a purified propylene oxide from a reaction product obtained from an epoxidation process, preferably, wherein propylene is epoxidized with hydrogen peroxide in the presence of a titanium-containing zeolitic catalyst. Advantageously, the process of this invention achieves a high efficiency of separation yielding a purified propylene oxide that is essentially devoid of methanol and water. In a preferred embodiment of the invention, the purified propylene oxide may be distilled to remove any residual aldehydes that may be present, resulting in a purified propylene oxide that meets commercial grade purity standards. More advantageously, the process of this invention accomplishes this efficient separation without undue loss of propylene oxide through side-reactions to propylene glycol or propylene glycol heavies. Most advantageously, the novel process of this invention can be integrated into a separation and purification scheme, described hereinafter, that results in a purified propylene oxide product of high quality being recovered from a crude epoxidation reaction product.

Accordingly, in a second aspect, this invention provides for an integrated process of obtaining a purified propylene oxide from a crude epoxidation reaction product, comprising:

(a) distilling a crude epoxidation reaction product comprising propylene oxide, methanol, water, acetaldehyde, and unreacted propylene under conditions sufficient to obtain a first bottoms stream comprising a portion of the methanol, water, and acetaldehyde, and a first overhead stream comprising propylene oxide and unreacted propylene and the balance of the methanol, water, and acetaldehyde;

(b) subjecting the first overhead stream from step (a) to distillation under conditions sufficient to remove substantially unreacted propylene and to obtain a second bottoms stream comprising from about 65 to 88 percent propylene oxide, from about 10 to about 35 percent methanol, less than about 0.5 percent water, from about 0.1 to about 0.5 percent acetaldehyde, and less than about 2 percent unreacted propylene, by weight;

(c) feeding the second bottoms stream from step (b) to the bottom section of an extractive distillation column and subjecting the stream to extractive distillation with water as an extractive solvent, under extractive distillation conditions sufficient to obtain a third bottoms stream comprising propylene oxide, water, and methanol; a third overhead or a side-cut stream comprising a purified propylene oxide containing residual acetaldehyde but essentially devoid of methanol, water, and unreacted propylene; and optionally a top stream comprising propylene; the yield loss of propylene oxide of step (c) being maintained at less than about 0.3 mole percent;

(d) optionally, recycling the third bottoms stream from step (c) to distillation step (a);

(e) optionally, recycling the top stream from step (c) to distillation step (b); and (f) optionally, distilling the third overhead or side-cut stream from step (c) to recover a purified propylene oxide meeting commercial grade purity standards.

In another aspect of this invention, the crude propylene oxide reaction product employed in the above-described separation and purification processes is obtained from a process comprising contacting propylene with hydrogen peroxide in a liquid phase in methanol solvent and in the presence of an epoxidation catalyst under epoxidation conditions sufficient to prepare a crude epoxidation product comprising propylene oxide, water, methanol, unreacted propylene, glycol and glycol ethers, and acetaldehyde. Unreacted hydrogen peroxide may also be present in the reaction product.

The aforementioned integrated process of this invention effects the separation and purification of a crude epoxidation reaction product comprising propylene oxide obtained in the epoxidation of propylene with hydrogen peroxide. Advantageously, the separation-purification process of this invention provides for a purified propylene oxide meeting commercial grade purity standards. More advantageously, the separation-purification process of this invention produces little, if any, loss of propylene oxide product through side-reactions with methanol or extractive solvent to form glycols and other heavies.

DRAWING

FIG. 1 illustrates a preferred embodiment of this invention wherein a crude propylene oxide reaction product, obtained from the epoxidation of propylene with hydrogen peroxide, is purified in a separation-purification unit comprising four distillation towers, as described in detail hereinafter.

DETAILED DESCRIPTION OF THE INVENTION

The novel process invention relates to a method of separating a purified propylene oxide from a propylene oxide epoxidation product comprising propylene oxide, methanol, water, acetaldehyde, and unreacted propylene. The process beneficially achieves this desired goal without unacceptable losses of propylene oxide to propylene glycol, glycol ethers and other glycol heavies. These byproducts can arise during epoxidation to prepare propylene oxide as well as during the process of separating the propylene oxide from the epoxidation reaction product. The process of this invention is concerned with maintaining low yield losses of propylene oxide to glycols during the separation of the propylene oxide from the epoxidation reaction mixture. In its broadest concept, the novel process comprises:

(a) introducing a propylene oxide reaction product comprising from about 65 to 88 percent propylene oxide, from about 10 to about 35 percent methanol, and less than about 0.5 percent water, by weight, into a bottom section of an extractive distillation zone;

(b) introducing water into an upper-half section of said extractive distillation zone;

(c) removing from said extractive distillation zone under extractive distillation conditions a bottoms stream comprising methanol, water, and propylene oxide;

(d) removing from said extractive distillation zone under extractive distillation conditions an overhead or side-cut stream comprising a purified propylene oxide essentially devoid of methanol and water; the extractive distillation conditions being sufficient to maintain a yield loss of propylene oxide of less than about 0.3 mole percent.

The phrase "essentially devoid of methanol" shall be taken to mean that the concentration of methanol in the overhead or side-cut distillate stream comprises no greater than about 50 parts per million (ppm) methanol, preferably, no greater than about 30 ppm, and more preferably, no greater than about 10 ppm methanol, by weight. The phrase "essentially devoid of water" shall be taken to mean that the concentration of water in the overhead or side-cut distillate stream comprises no greater than 100 ppm water, by weight.

In a preferred embodiment, this invention provides for a novel process of separating a purified propylene oxide from a propylene oxide epoxidation product, comprising:

(a) introducing an epoxidation product comprising from about 65 to 88 percent propylene oxide, from about 10 to 35 percent methanol, and less than about 0.5 percent water, by weight, to an extractive distillation zone at about the first to fifth theoretical stage measured from the bottom of the extractive distillation zone;

(b) introducing water to the upper-half section of the extractive distillation zone;

(c) maintaining the extraction distillation zone at a bottoms temperature of about 55° C. to 75° C., so as to remove from said extractive distillation zone under extractive distillation conditions a bottoms stream comprising from about 20 to 40 percent propylene oxide, from about 10 to 25 percent water, and from about 40 to 60 percent methanol, by weight, and;

(d) removing from said extractive distillation zone an overhead or side-cut stream comprising greater than about 99 percent propylene oxide, no greater than about 100 ppm water, and no greater than about 50 ppm methanol, by weight; the extractive distillation maintaining a yield loss of propylene oxide of less than about 0.3 mole percent, preferably, less than about 0.2 mole percent, and more preferably, less than about 0.15 mole percent.

In another related aspect of this invention, the overhead or side-cut stream comprising propylene oxide essentially devoid of methanol and water may be further distilled to remove any residual aldehydes that may be present, so as to recover a propylene oxide product meeting commercial grade purity standards, such that the propylene oxide product comprises greater than 99.95 percent propylene oxide and contains no greater than 100 ppm water, no greater than 10 ppm methanol, and no greater than 30 ppm aldehydes.

In a second aspect, this invention is an integrated process of preparing a purified propylene oxide comprising:

(a) distilling a crude propylene oxide reaction product comprising propylene oxide, methanol, water, acetaldehyde, and unreacted propylene to obtain a first bottoms stream comprising a portion of the methanol, water, and acetaldehyde and a first overhead stream comprising propylene oxide, unreacted propylene, and the balance of methanol, water, and acetaldehyde;

(b) distilling the first overhead stream of step (a) to remove substantially unreacted propylene as a second overhead stream and to recover a second bottoms stream comprising from about 65 to 88 percent propylene oxide, from about 10 to 35 percent methanol, less than about 0.5 percent water, from about 0.1 to 0.5 percent acetaldehyde, and less than about 2 percent unreacted propylene, by weight;

(c) feeding the second bottoms stream obtained from step (b) to the bottoms section of an extractive distillation column and subjecting said stream to extractive distillation with water as the extraction solvent under extractive distillation conditions sufficient to obtain a third bottoms stream comprising propylene oxide, water, and methanol; and a third overhead or side-cut stream comprising a purified propylene oxide containing residual acetaldehyde but essentially devoid of water, methanol, and propylene; and optionally, a top stream comprising unreacted propylene; wherein the yield loss of propylene oxide in the extractive distillation step (c) is less than 0.3 mole percent;

(d) optionally, recycling the third bottoms stream from step (c) to step (a);

(e) optionally, recycling the top stream from step (c) to step (b); and (f) optionally, distilling the third overhead or side-cut stream from step (c) to obtain a purified propylene oxide of commercial grade purity.

In step (a) the phrases "a portion of the methanol, water, and acetaldehyde" and "the balance of the methanol, water, and acetaldehyde" are described fully hereinbelow, wherein the concentration ranges of methanol, water, and acetaldehyde in the first bottoms and first overhead streams are set forth. The term "residual acetaldehyde" shall be taken to mean a concentration of acetaldehyde of less than 1 percent, preferably, less than about 0.4 percent, by weight. In step (c), the phrase "essentially devoid of methanol" shall be taken to mean that the concentration of methanol in the overhead or side-cut distillate stream comprises no greater than about 50 parts per million (ppm) methanol, by weight. In step (c) the phrase "essentially devoid of water" shall be taken to mean that the concentration of water in the overhead or side-cut stream comprises no greater than 100 ppm, by weight. A purified propylene oxide meeting commercial grade purity standards shall consist essentially of 99.95 percent or greater of propylene oxide, but no greater than 100 ppm water, no greater than 10 ppm methanol, and no greater than 30 ppm aldehydes, by weight.

In a more preferred embodiment, the extractive distillation step (c) is conducted at a bottoms temperature greater than about 55° C. and less than about 75° C. In another preferred embodiment, distillation step (a) to remove methanol and water is conducted at a reflux to distillate ratio less than 10/1, more preferably, less than about 5/1, and most preferably, less than about 2/1.

The aforementioned crude propylene oxide reaction product is preferably obtained by contacting propylene with hydrogen peroxide in a liquid phase in a solvent, preferably methanol, and in the presence of an epoxidation catalyst under epoxidation conditions sufficient to prepare the crude propylene oxide reaction product comprising propylene oxide, water, solvent (methanol), glycols, acetaldehyde, and unreacted propylene. Other components may be present in the crude epoxidation product including, for example, lights, such as propane, and by-products, such as propionaldehyde and acetone. Generally, it is desirable to manipulate the epoxidation process conditions to minimize the production of by-products, such as glycols. Typically, the epoxidation catalyst is filtered from the crude propylene oxide reaction product prior to initiating the separation-purification scheme of this invention.

In reference to FIG. 1 herein, the novel process of this invention is illustrated in a preferred embodiment. A catalyst-free crude epoxidation reaction product, obtained from the epoxidation of propylene with hydrogen peroxide in methanol solvent and comprising propylene oxide, methanol, water, acetaldehyde, unreacted propylene, and optionally glycols and glycol ethers formed during the epoxidation process, is fed via line S1 into a first distillation tower T1 for the purpose of removing bulk methanol and water, and any glycols and glycol ethers formed during the epoxidation process. From the bottom of the first distillation tower there results a first bottoms stream S3 containing predominantly methanol and water and minor amounts of glycol, glycol ethers, acetaldehyde and other oxygenated byproducts. Only a portion of the acetaldehyde is typically obtained in the first bottoms stream with the methanol and water. First bottoms stream S3 is typically sent to a methanol recovery unit (not shown in figure) for separation of methanol from water, glycols, and any other impurities. The recovered methanol can be recycled as solvent to the epoxidation process. The recovered water can be disposed or recycled to the extractive distillation tower T3, as described hereinafter. From distillation tower T1, a first overhead stream, S2, containing propylene oxide, the balance of water, methanol, and acetaldehyde, unreacted propylene and typically any propane present, is obtained and fed to distillation tower T2. A second overhead stream S4, obtained from distillation tower T2 and comprising propylene and optionally other lights, such as propane and oxygen, is recycled, after propane and oxygen removal, as raw material back to the epoxidation reactor (not shown in figure). A second bottoms stream S5, obtained from second distillation tower T2 and comprising propylene oxide, water, methanol, acetaldehyde, and less then 2% of propylene and propane, is thereafter subjected to extractive distillation by introducing second bottoms stream S5 into the bottom section of an extractive distillation tower T3. An extractive distillation solvent, in this instance, water, is introduced into an upper-half section of extractive distillation tower T3. Thereafter, under extractive distillation conditions a third bottoms stream, S7, comprising propylene oxide, water, methanol, and minor amount of glycols is removed from said extractive distillation tower T3; stream S7 optionally may be recycled to first distillation tower T1 for recycling to the separation-purification system. Additionally, in one preferred embodiment an overhead distillate stream S6, comprising propylene oxide, unreacted propylene and optionally other lights, such as propane, is obtained from extractive distillation tower T3. Stream S6 may be recycled to distillation tower T2 for recovery of propylene oxide, unreacted propylene and lights. Additionally, from extractive distillation tower T3 a third overhead stream or side-cut stream, S8, is obtained comprising a purified propylene oxide optionally containing residual acetaldehyde, the stream being essentially devoid of methanol and water. Third overhead stream or side-cut stream S8 is fed to distillation tower T4 to recover a fourth overhead stream S9 comprising acetaldehyde, a fourth bottoms stream S11 (not shown) comprising propylene oxide and minor amounts of heavy impurities, which is optionally recycled to tower T3, and a fifth bottoms or side-cut stream S10 comprising a highly purified propylene oxide meeting commercial grade purity standards.

In accordance with the process of this invention, the crude epoxidation reaction product generally is obtained by epoxidizing propylene with hydrogen peroxide or an equivalent peroxide in the presence of an epoxidation catalyst in a reaction medium. Typically, the reaction medium contains a solvent, preferably chosen as having a boiling point between the boiling points of propylene oxide and water. Suitable solvents include, inter alia, alcohols, for example, methanol, ethanol, or tert-butanol; ethers, for example, tetrahydrofuran or 1,2-dimethylethane; and ketones, for example, acetone. In the process of this invention, methanol is preferably used as the solvent. Hydrogen peroxide is preferably employed as the oxidant and is usually provided as aqueous solution in a concentration from about 10 to 70 weight percent, preferably, about 30 to 45 weight percent. Propylene may be used mixed with propane, typically in an amount from between about 0 and 10 volume percent propane. Propylene is fed in excess relative to hydrogen peroxide. Typically on a molar basis, the propylene to hydrogen peroxide ratio is greater than about 2.5/1. The epoxidation catalyst, which typically comprises a titanium-containing zeolite, such as titanium silicalite, may be provided in a fixed-bed or alternatively suspended in the reaction medium. The epoxidation reaction is typically carried out at temperatures between about 0° C. and 80° C. and at elevated pressures of about 10 bar (1,000 kPa) to 20 bar (2,000 kPa). Such processes are more fully described in the art, for example, as disclosed in WO-A1-09/14298. The epoxidation catalyst is typically separated from the crude epoxidation reaction product by filtration or other such means prior to implementation of the separation-purification process of this invention. Typically, the catalyst-free crude epoxidation reaction product comprises the following components, given in percentages by weight:

Propylene oxide, about 3 to 35%
   Methanol, about 35 to 80%
   Water, about 8 to 40%
   Acetaldehyde, about 0.01 to 0.1%
   Propylene, about 0.5 to 15%
   Propylene glycol and glycol heavies, about 0.1 to 1%

With reference again to FIG. 1, the catalyst-free crude epoxidation reaction product, in stream S1, is fed to distillation tower T1 and subjected to fractionation under conditions sufficient to remove substantially bulk methanol and water, glycols, a portion of the acetaldehyde, and other oxygenated impurities. Distillation tower T1 typically comprises from greater than about 15 to less than about 40 theoretical stages. The crude epoxidation reaction product is generally introduced into the upper ⅓ of the tower. The distillation operates generally at a temperature in the top of the tower greater than about 40° C. The distillation operates generally at a bottoms temperature of less than about 100° C. The column top pressure is typically greater than about 1 bar abs (100 kPa). The column pressure is typically less than about 2.5 bar abs (250 kPa). Typically, tower T1 is operated at a reflux to distillate ratio of less than about 10/1, more preferably less than about 5/1, and most preferably, less than about 2/1.

A bottoms stream S3 comprising a fraction of the original methanol, water, and acetaldehyde, and essentially all of the glycols and glycol ethers produced in the epoxidation process is obtained from tower T1. More specifically, greater than about 85 percent, by weight, of the original methanol fed with the crude epoxidation product is removed in bottoms stream S3, while the remainder of the methanol remains with overhead stream S2, also obtained from tower T1. More specifically, greater than about 90 percent and less than about 100 percent, by weight, of the original methanol fed to tower T1 is removed in bottoms stream S3, while the balance remains in propylene oxide overhead stream S2. Typically, greater than about 95 percent, and preferably, greater than about 99 percent, by weight, of the water fed with the crude epoxidation product to tower T1 is removed with the bottoms stream S3. According to the invention, typically more than about 95 percent, preferably, more than about 98 percent, and more preferably, more than about 99 percent of the propylene oxide fed with the crude epoxidation product mixture to tower T1 is contained in the overhead stream S2. The acetaldehyde is split between overhead stream S2 and bottoms stream S3. Typically, from about 30 to about 60 percent of the total acetaldehyde present in the crude epoxidation reaction product remains in the propylene oxide overhead stream S2; whereas the remainder of the acetaldehyde is removed with the bulk methanol and water in bottoms stream S3. Accordingly, overhead stream S2 comprises propylene oxide, methanol, a significantly reduced quantity of water, any unreacted propylene, and roughly about one-half of the acetaldehyde fed.

Bottoms stream S3 comprising methanol, water, and a portion of the acetaldehyde and the overall amount of glycols fed, can be fractionated in a methanol recovery unit (not shown in figure) to recover methanol for recycle to the epoxidation process. Water obtained from the methanol recovery unit may be disposed as waste or partially cycled to distillation tower T3 for use as an extractive distillation solvent.

Referring again to FIG. 1, following the removal of bulk methanol and water in distillation tower T1, the overhead distillate stream S2 is fed to lights distillation tower T2 for the purpose of separating unreacted propylene and other lights, including propane. The lights distillation tower T2 operates under conventional conditions for such a separation, including generally a temperature greater than about −25° C., and preferably, greater than about −20° C. Typically, the lights tower T2 operates at a temperature less than about 5° C., and preferably, less than about 0° C. The top pressure of distillation tower T2 is typically greater than about 2 bar abs (200 kPa) and less than about 5 bar abs(500 kPa). From the second distillation tower T2, an overhead stream S4 comprising propylene, propane, and other lights is recovered, which may optionally be recycled, typically after further purification, to the epoxidation reactor wherein propylene is consumed to form propylene oxide. Following the separations of bulk methanol, bulk water, unreacted propylene and other lights, and glycols and glycol heavies produced in the epoxidation process, the propylene oxide epoxidation reaction product obtained from tower 12 as bottoms stream S5 typically comprises a composition having the following components, in percentages by weight:

Propylene oxide, about 65 to 88%
Methanol, about 10 to 35%
Water, less than about 0.5%
Acetaldehyde, about 0.1 to 0.5%
Propylene, less than about 2%

Referring again to FIG. 1, bottoms stream S5 obtained from lights distillation tower T2 is fed to an extractive distillation tower T3, designed appropriately for a high efficiency separation of propylene oxide from methanol and water. In a preferred embodiment, the extractive distillation tower T3 contains greater than about 30 theoretical stages, and preferably, greater than about 50 theoretical stages. In a preferred embodiment, the extractive distillation tower T3 contains less than about 100 theoretical stages, and preferably, less than about 80 theoretical stages. The use of one extractive distillation column is preferred for economic reasons and ease of design; but the invention should not be limited to such a design. The propylene oxide reaction product, obtained as bottoms stream S5 and typically comprising from about 65 to 88 percent propylene oxide, from about 10 to about 35 percent methanol, less than about 0.5 percent water, from about 0.1 to about 0.5 percent acetaldehyde, and less than about 1 percent propylene, by weight, is beneficially introduced into the bottom section of extractive distillation tower T3. For the purposes of this invention, the term "bottom section" shall be taken to mean the bottom ¼ of the column, measured as theoretical stages from the bottom to the top of the extractive distillation zone. Preferably, the epoxidation reaction product is introduced into the extractive distillation column at a point between about the first and fifth theoretical stage measured from the bottom. The extractive solvent, which in this case is water, is introduced at a point in the upper-half of the column. A purified propylene oxide distillate, shown as stream S8, is removed from the top or as a side-cut taken from about theoretical stages 2 to 6 of tower T3, measured from the top down towards the bottom of the column. If the purified propylene oxide is taken as a side-cut, then the propylene reach in top product, shown as stream S6 in FIG. 1, optionally may be recycled to a propylene recovery system, for example, the second stage distillation tower T2 described herein, for recycling of propylene to the epoxidation process.

The extractive distillation operating parameters can be varied, provided that the desired degree of purification of propylene oxide is effected. A suitable water to purified propylene oxide (PO) stream ratio (water/feed S8 ratio) is important in achieving optimum results in the extractive distillation. Generally, the water to purified PO stream ratio will be less than about 1:20, preferably, less than about 1:15 by weight. Generally, the water to purified PO stream ratio will be greater than about 1:5, and preferably, greater than about 1:8, by weight. Likewise, a suitable reflux to distillate ratio is important in achieving optimum results. For the case that purified propylene oxide is taken as top stream from the column T3, the reflux ratio generally will be greater than about 3:1, preferably, greater than about 4:1; but generally less than about 10:1, and preferably, less than about 3:1, by weight.

The overhead temperature of extractive distillation column, shown as tower T3 in FIG. 1, is typically maintained in a range that is greater than about 35° C. and less than about 45° C. The bottoms temperature of the extractive distillation tower is important in maintaining a propylene oxide yield loss typically of less than about 0.3 mole percent. Typically, the bottoms temperature of the extractive distillation tower is maintained in a range that is greater than about 55° C. and less than about 75° C. Typically, the extractive distillation tower is operated at a pressure greater than about 0.5 bar (50 kPa), and preferably, greater than about 1 bar (100 kPa). Typically, the extractive distillation tower is operated at a pressure less than about 2 bar (200 kPa), and preferably, less than about 1.6 bar (160 kPa).

By operating the extractive distillation tower under the aforementioned conditions, a bottoms stream is obtained that typically comprises the following components, in percentages by weight:

Propylene Oxide, about 20-40%
Methanol, about 40-60%
Water, about 10-25%

Propylene glycol, about 0.05-0.3%
Other glycols and heavies, about 0.1-0.2%

Preferably, the bottoms stream, removed as stream S7 from the extractive distillation tower T3, is combined with the crude propylene oxide feed in stream S1 and recycled to first distillation tower T1 for recycling through the separation-purification process. Significantly, the total yield loss of propylene oxide to propylene glycol and other glycol heavies, obtained over the total process, is no greater than about 0.3 mole percent, preferably, no greater than about 0.2 mole percent, and more preferably, no greater than about 0.15 mole percent. As mentioned hereinbefore, the term "yield loss of propylene oxide" refers to the mole percentage of propylene oxide lost in the extraction process to glycols and glycol heavies, based on the total moles of propylene oxide fed to the extractive distillation.

By operating the extractive distillation tower under the aforementioned process conditions, a purified propylene oxide stream is obtained as an overhead or side-cut stream, which typically comprises the following components, in percentages by weight:

Propylene Oxide, greater than about 99.5%
Methanol, no greater than about 50 ppm
Water, no greater than about 100 ppm,
Acetaldehydes, no greater than 1%

Typically, however, the acetaldehyde in third overhead or side-cut stream is greater than about 0.01 weight percent. Preferably, the acetaldehyde is less than about 0.4 weight percent.

Optionally, the purified propylene oxide obtained from the extractive distillation tower T3 may be distilled in a conventional distillation column to remove residual reaction by-products, in particular acetaldehyde, to yield a purified propylene oxide that meets commercial grade standards of purity. This finishing distillation can be conducted in a tower having from about 40 to 80 theoretical stages and operating at a temperature of between about 35° C. and 45° C., preferably about 40° C., and a top column pressure of between about 1 bar abs (100 kPa) and about 3 bar abs (300 kPa), preferably, about 2 bar abs (200 kPa). The feed point can be, for example, at about the ⅓ point of the column, measuring from the top, plus or minus about 5 theoretical stages. The highly purified propylene oxide is obtained as bottoms stream S10. For the purposes of this invention, the "bottoms" cut may be taken from the bottom tray as well from the last 5 trays of the column. The purified propylene oxide, taken as stream S10, consists essentially of the following components, in percentages by weight:

Propylene oxide, greater than 99.95%
Water, no greater than 100 ppm
Methanol, no greater than 10 ppm
Acetaldehyde, no greater than 30 ppm As seen from the above description, the process of this invention advantageously produces a purified propylene oxide meeting commercial grade purity requirements without undue loss of propylene oxide to propylene glycol and other glycol heavies.

Throughout the description hereinabove, the words "no greater than" are used in reference to specified concentrations of particular product components. For the purposes of this invention, the words "no greater than" shall be taken to mean a value equal to or less than the specified value. For example, the words "no greater than 100 ppm water" shall be taken to mean equal to or less than 100 ppm water.

The invention will be further clarified by a consideration of the following example, which is intended to be purely exemplary of the use of the invention. Other embodiments of the invention will be apparent to those of skill in the art from a consideration of this specification or practice of the invention as disclosed herein.

EXAMPLE 1

With reference to FIG. 1, a crude reaction product mixture resulting from the epoxidation of propylene with hydrogen peroxide in methanol solvent in the presence of titanium silicalite catalyst was filtered to remove the catalyst and thereafter fed as stream S1 to distillation tower T1. The crude epoxidation product had the composition shown in Table 1, in percentages by weight:

TABLE 1

Crude Epoxidation Product

| Component | Wt % |
|---|---|
| Propylene Oxide | 5.5 |
| Methanol | 78.1 |
| Water | 9.3 |
| Propylene | 5.3 |
| Propane | 0.8 |
| Propylene glycol & glycol ethers | 0.6 |
| Acetaldehyde | 0.04 |
| Other impurities | 0.36 |

The operating conditions for tower T1 were as follows: top temperature, 40° C.; top pressure, 2 bar (200 kPa); bottom temperature, 89° C. From tower T1 was obtained a first bottoms fraction, shown as stream S3, containing methanol, water, acetaldehyde, and heavy components, such as glycol and glycol ethers; and a first light fraction as stream S2 containing propylene oxide, unreacted propylene, and the balance of methanol, water, and acetaldehyde. The light fraction was further fractionated in a second column (T2) containing 20 theoretical stages and operating at −12.5° C. on the top and 4 bar (400 kPa) to remove unreacted propylene as second light stream S4. A second bottoms fraction was obtained as bottoms steam S5 having the following composition, in percentages by weight, as shown in Table 2:

TABLE 2

Bottoms Stream S5

| Component | Bottoms (wt %) |
|---|---|
| Propylene Oxide | 86.69 |
| Methanol | 10.25 |
| Water | 0.12 |
| Propylene | 0.62 |
| Acetaldehyde | 0.26 |

The propylene oxide reaction product having the composition shown in Table 2, obtained as second bottoms stream S5, was fed to an extractive distillation column (T3) containing 60 theoretical stages. The feed point of the reaction product was at theoretical stage 2 from the bottom of the column. Water was used as an extractive solvent, being added at theoretical stage 30, measured from the bottom to the top of the column. The bottom temperature of the column was maintained at 61° C. The top temperature was maintained at 37° C. The weight ratio of water as extractive solvent to purified propylene oxide was 1:12.5. The top column pressure was maintained at 1.3 bar abs (130 kPa). A purified propylene oxide stream was removed as stream S8 as a side cut from theoretical stage 3 of extractive distillation tower T3, measured from the top of the column to the bottom. A bottoms stream was obtained as stream S7. The compositions of the overhead stream S8 and bottoms stream S7 were found to be the following, as shown in Tables 3 and 4, respectively:

TABLE 3

Overheads Stream S8

| Component | Overheads (wt %) |
|---|---|
| Propylene Oxide | 99.700 |
| Methanol | 0.001 |
| Water | 0.006 |
| Propylene | 0.003 |
| Acetaldehyde | 0.285 |

TABLE 4

Bottoms Stream S7

| Component | Bottoms (wt %) |
|---|---|
| Propylene Oxide | 32.52 |
| Methanol | 45.20 |
| Water | 20.65 |
| Propylene glycol | 0.25 |
| Glycol ethers | 0.15 |
| Acetaldehyde | 0.075 |

From Table 3 it is seen that the overhead stream S8 obtained from the extractive distillation column contained propylene oxide essentially devoid of methanol and water (methanol only 10 ppm; water only 60 ppm). From Table 4 it is seen that the bottoms stream S7 contained predominantly propylene oxide, methanol, and water. The quantity of propylene oxide lost to propylene glycol corresponded to 0.125 kg/h, equivalent to 0.25 weight percent. The quantity of propylene oxide lost to glycol ethers and other glycol heavies corresponded to 0.075 kg/h, equivalent to 0.15 weight percent. At a production rate of 125 kg/h propylene oxide, the total loss to propylene glycol and glycol ethers was evaluated to be 0.115 mole percent, based on the total moles of propylene oxide and glycols produced from the extractive distillation.

The bottoms stream S7 obtained from extractive distillation tower T3 was recycled to stream S1 feeding to tower T1. The purified propylene oxide stream, taken as overheads stream S8 from the extractive distillation column T3, can be fed to a finishing distillation tower T4 to remove low boiling components, particularly acetaldehyde. The finishing distillation was conducted in a tower having 60 theoretical plates and operating at a temperature of 40° C. and a top column pressure of 2 bar (200 kPa). The feed point was theoretical stage 15 measured from the top of the column to the bottom. A finished propylene oxide, which meets commercial grade purity standards, was obtained as bottoms product stream S10 having the composition as shown in Table 5.

TABLE 5

Finished Propylene Oxide

| Component | Overhead[1] |
|---|---|
| Propylene Oxide | 99.97 wt % |
| Methanol | 10 ppm |
| Water | 100 ppm |
| Acetaldehyde | 30 ppm |

[1]Maximum observed for methanol, water, acetaldehyde,

The invention claimed is:

1. A process of separating a purified propylene oxide from a propylene oxide reaction product, the process comprising:
   (a) introducing a reaction product comprising from about 65 to 88 percent propylene oxide, from about 10 to 35 percent methanol, and less than about 0.5 percent water into a bottom section of an extractive distillation zone;
   (b) introducing water into an intermediate section of said extractive distillation zone;
   (c) removing from said extractive distillation zone under distillation conditions a bottoms stream comprising propylene oxide, water, and methanol,
   (d) removing from said extractive distillation zone under distillation conditions, an overhead or side-cut stream, comprising a purified propylene oxide essentially devoid of methanol and water; the extractive distillation conditions being sufficient to maintain a yield loss of propylene oxide of less than about 0.3 mole percent.

2. The process of claim 1 wherein the propylene oxide reaction product fed to the extractive distillation zone additionally comprises less than 2 percent propylene and/or from about 0.1 to 0.5 percent acetaldehyde, by weight.

3. The process of claim 1 wherein the extractive distillation zone contains from greater than about 30 to less than about 100 theoretical stages.

4. The process of claim 1 wherein the propylene oxide reaction product is fed to the bottom ¼ of the extractive distillation zone, measured as theoretical stages from the bottom to the top of the extractive distillation zone.

5. The process of claim 1 wherein water is introduced into the upper-half section of the extractive distillation zone.

6. The process of claim 1 wherein the extractive distillation zone is operated at a water to purified propylene oxide (PO) stream ratio of less than about 1:20 and greater than about 1:5, by weight.

7. The process of claim 1 wherein the distillation zone is operated at an overhead temperature of greater than about 35° C. and less than about 45° C.

8. The process of claim 1 wherein the distillation zone is operated at a bottoms temperature of greater than about 55° C. and less than about 75° C.

9. The process of claim 1 wherein the distillation zone is operated at a pressure of greater than about 0.5 bar (50 kPa) and less than about 2 bar (200 kPa).

10. The process of claim 1 to 9 wherein a bottoms stream is obtained that comprises the following components, in percentages by weight: from about 20 to 40 percent propylene oxide, from about 40 to 60 percent methanol, from about 10 to 25 percent water, from about 0.05 to 0.3 percent propylene glycol, and from about 0.1 to 0.2 percent glycol ethers.

11. The process of claims 10 wherein the propylene oxide obtained as an overhead or side-cut stream from the extractive distillation zone is distilled to yield a purified propylene oxide meeting commercial grade purity standards.

12. The process of claim 11 wherein the purified propylene oxide meeting commercial grade standards of purity is comprised of the following components, in percentages by weight: propylene oxide, greater than 99.95 percent; no greater than 100 ppm water; no greater than 10 ppm methanol; and no greater than 30 ppm aldehydes.

13. The process of claim 1 wherein the purified propylene oxide overhead or side-cut stream comprises greater than about 99.5 percent propylene oxide in percentage by weight.

14. The process of claim 1 wherein the yield loss of propylene oxide to propylene glycol and glycol ethers is less than about 0.2 mole percent.

15. The process of claim 1 wherein the propylene oxide reaction product is obtained from a catalyzed process comprising contacting propylene with hydrogen peroxide in a liquid phase in methanol solvent under epoxidation conditions.

16. The process of claim 1 wherein the first distillation zone is operated with from greater than 15 to less than 40 theoretical stages, at a top temperature greater than 40° C. and a bottoms temperature less than 100° C., and at a reflux to distillate ratio of less than 10:1.

17. A process of separating a purified propylene oxide from an epoxidation reaction product, the process comprising:
(a) distilling in a first distillation zone a crude propylene oxide reaction product comprising propylene oxide, methanol, water, acetaldehyde, and unreacted propylene to obtain a first bottoms stream comprising a portion of the methanol, water, and acetaldehyde, and an overhead stream comprising propylene oxide and unreacted propylene and the balance of the methanol, water, and acetaldehyde;
(b) distilling in a second distillation zone the overhead stream of step (a) to remove unreacted propylene and to recover a second bottoms stream comprising from about 65 to 88 percent propylene oxide, from about 10 to 35 percent methanol, less than about 0.5 percent water, and from about 0.1 to 0.5 percent acetaldehyde, and less than 2 percent unreacted propylene, by weight;
(c) feeding the second bottoms stream obtained from step (b) to the bottoms section of an extractive distillation column and subjecting said stream to extractive distillation with water as the extraction solvent under extractive distillation conditions sufficient to obtain a third bottoms stream comprising propylene oxide, water, and methanol; optionally, a top stream comprising unreacted propylene; and a third overhead distillate or side-cut stream comprising a purified propylene oxide containing residual acetaldehyde but essentially devoid of water, methanol, and unreacted propylene, while maintaining a yield loss of propylene oxide in the extractive distillation step (c) of less than 0.3 mole percent;
(d) optionally, recycling the third bottoms stream from step (c) to step (a);
(e) optionally, recycling the top stream from step (c) to step (b); and
(f) optionally, distilling the third overhead or side-cut distillate stream from step (c) to remove any residual acetaldehyde and to obtain a purified propylene oxide of commercial grade purity.

18. The process of claim 17 wherein the crude propylene oxide reaction product is obtained in an epoxidation process comprising reacting propylene with hydrogen peroxide in the presence of a titanium-containing catalyst.

19. The process of claim 17 wherein the crude propylene oxide reaction product comprising the following composition in percentages by weight: from about 3 to 35 percent propylene oxide, from about 35 to 80 percent methanol, from about 8 to 40 percent water, from about 0.5 to 15 percent propylene, and less than about 0.1 percent acetaldehyde.

20. The process of claim 18 wherein the epoxidation catalyst is a titanium silicate.

21. The process of claim 17 wherein the second distillation zone is operated at a temperature greater than −25° C. and less than 5° C. at a pressure greater than 2 bar abs (200 kPa) and less than 5 bar abs (500 kPa).

22. A process of separating a purified propylene oxide product obtained from the reaction of propylene with hydrogen peroxide in the presence of a titanium-containing catalyst, the process comprising:
(a) introducing an epoxidation product comprising from about 65 to 88 percent propylene oxide, from about 10 to 35 percent methanol, and less than about 0.5 percent water, by weight, to about the first to fifth theoretical stage measured from the bottom of an extractive distillation zone;
(b) introducing water into the upper-half of the extractive distillation zone;
(c) maintaining the extractive distillation zone at a bottoms temperature greater than about 55° C. and less than about 75° C., so as to remove from said extractive distillation zone under extractive distillation conditions a bottoms stream comprising from about 20 to 40 percent propylene oxide, from about 10 to 25 percent water, and from about 40 to 60 percent methanol, by weight, and;
(d) removing from said extractive distillation zone an overhead or side-cut stream comprising greater than 99.5 percent propylene oxide, no greater than about 100 ppm water, and no greater than about 50 ppm methanol, by weight; while maintaining a yield loss of propylene oxide of less than about 0.3 mole percent.

23. A process of separating a purified propylene oxide from a propylene oxide reaction product, the process comprising:
(a) introducing a reaction product comprising from about 65 to 88 percent propylene oxide, from about 10 to 35 percent methanol, and less than about 0.5 percent water and additionally comprising less than 2 percent propylene and/or from about 0.1 to 0.5 percent acetaldehyde, by weight, into the bottom ¼ of an extractive distillation zone, measured as theoretical stages from the bottom to the top of the extractive distillation zone, the extractive distillation zone containing from greater than about 30 to less than about 100 theoretical stages;
(b) introducing water into an intermediate section of said extractive distillation zone;
(c) removing from said extractive distillation zone under distillation conditions a bottoms stream comprising propylene oxide, water, and methanol,
(d) removing from said extractive distillation zone under distillation conditions, an overhead or side-cut stream, comprising a purified propylene oxide essentially devoid of methanol and water; wherein the distillation zone is operated at an overhead temperature of greater than about 35° C. and less than about 45° C., at a bottoms temperature of greater than about 55° C. and less than about 75° C., and a pressure of greater than about 0.5 bar (50 kPa) and less than about 2 bar (200 kPa), the extractive distillation conditions being sufficient to maintain a yield loss of propylene oxide of less than about 0.3 mole percent.

* * * * *

UNITED STATES PATENT AND TRADEMARK OFFICE
CERTIFICATE OF CORRECTION

PATENT NO. : 7,594,979 B2                                           Page 1 of 1
APPLICATION NO. : 10/541171
DATED : September 29, 2009
INVENTOR(S) : Patrascu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 906 days.

Signed and Sealed this

Twenty-eighth Day of September, 2010

David J. Kappos
*Director of the United States Patent and Trademark Office*